(12) United States Patent
Harrington et al.

(10) Patent No.: US 6,712,810 B2
(45) Date of Patent: *Mar. 30, 2004

(54) METHOD AND APPARATUS FOR TUBAL OCCLUSION

(75) Inventors: Douglas C. Harrington, Redwood City, CA (US); Victoria E. Carr-Brendenl, Redwood City, CA (US); Brett S. Bowman, Redwood City, CA (US)

(73) Assignee: Adiana, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 09/810,761

(22) Filed: Mar. 16, 2001

(65) Prior Publication Data

US 2001/0016738 A1 Aug. 23, 2001

Related U.S. Application Data

(63) Continuation of application No. 09/241,790, filed on Feb. 1, 1999, now Pat. No. 6,309,384.

(51) Int. Cl.[7] .............................................. A61B 18/04
(52) U.S. Cl. ......................... 606/28; 128/831; 128/833
(58) Field of Search .................. 607/138; 128/830–833, 128/898; 606/41–50

(56) References Cited

U.S. PATENT DOCUMENTS

| | | | | |
|---|---|---|---|---|
| 2,102,270 A | 12/1937 | Hyams | ................... | 128/303.17 |
| 3,680,542 A | 8/1972 | Cimber | ...................... | 128/1 R |
| 3,805,767 A | 4/1974 | Erb | ............... | 128/1 R |
| 3,840,016 A | 10/1974 | Lindemann | ............ | 128/303.17 |
| 3,858,571 A | 1/1975 | Rudolph | ...................... | 128/1 R |
| 3,858,586 A | 1/1975 | Lessen | ........................ | 606/49 |
| 3,918,431 A | 11/1975 | Sinnreich | .................... | 128/1 R |
| 3,938,527 A | 2/1976 | Rioux et al. | ........... | 128/303.17 |
| 3,953,566 A | 4/1976 | Gore | .......................... | 264/288 |
| RE29,345 E | 8/1977 | Erb | ............................. | 128/1 R |
| 4,057,063 A | 11/1977 | Gieles et al. | .......... | 128/303.17 |
| 4,474,179 A | 10/1984 | Koch | ..................... | 128/303.17 |
| 4,606,336 A | 8/1986 | Zeluff | ......................... | 128/831 |
| 4,700,701 A | 10/1987 | Montaldi | ..................... | 606/28 |

(List continued on next page.)

FOREIGN PATENT DOCUMENTS

| | | |
|---|---|---|
| WO | WO 96/40023 | 12/1996 |
| WO | WO 96/40024 | 12/1996 |

OTHER PUBLICATIONS

Sahwi, The Leukocytic Response to an Intrauterine Foreign Body in the Rabbit, 22 Fertility and Sterility 398 (Jun. 1971).

Coleman, The Foreign Body Reaction: A Chronic Inflammatory Response, 8 J. Biomed. Mater. Res. 199–211 (1974).

Pollack, Wound Healing: A Review, 5:5 J. Dermatol. Surg. Oncol. 389 (May 1979).

(List continued on next page.)

*Primary Examiner*—Linda C. M. Dvorak
*Assistant Examiner*—David M. Ruddy
(74) *Attorney, Agent, or Firm*—K. David Crockett, Esq.; Crockett & Crockett

(57) ABSTRACT

Methods and devices for occlusion of the fallopian tubes of a woman. The method involves thermally damaging the lining of the utero-tubal junction with relatively low power, followed by placement of a reticulated foam plug. In one embodiment, vascularized tissue grows into the plug and prevents or discourages formation of scar tissue around the plug. Another embodiment with a relatively small foam pore size encourages formation of a vascularized capsule around the plug. The presence of this vascularized capsule limits the patient's foreign body response, so that the capsule does not constrict around the plug. Also presented is a catheter designed for wounding the epithelial layer of the utero-tubal junction, and a method of using the catheter to form a long yet shallow lesion in the utero-tubal junction.

32 Claims, 9 Drawing Sheets

(2 of 9 Drawing Sheet(s) Filed in Color)

U.S. PATENT DOCUMENTS

| | | | |
|---|---|---|---|
| 4,834,091 A | 5/1989 | Ott | 128/303.1 |
| 4,966,597 A | 10/1990 | Cosman | 606/50 |
| 5,009,655 A | 4/1991 | Daignault, Jr. et al. | 606/7 |
| 5,095,917 A | 3/1992 | Vancaillie | 128/831 |
| 5,122,137 A | 6/1992 | Lennox | 606/40 |
| 5,147,353 A | 9/1992 | Everett | 606/15 |
| 5,152,784 A | 10/1992 | Tsilibary | 623/1 |
| 5,167,658 A | 12/1992 | Ensslin | 606/34 |
| 5,303,719 A | 4/1994 | Wilk et al. | 128/898 |
| 5,556,396 A | 9/1996 | Cohen et al. | 606/42 |
| 5,569,245 A | 10/1996 | Guglielmi et al. | 606/49 |
| 5,569,462 A | 10/1996 | Martinson et al. | 424/424 |
| 5,589,176 A | 12/1996 | Seare, Jr. | 424/400 |
| 5,601,600 A | 2/1997 | Ton | 606/206 |
| 5,605,693 A | 2/1997 | Seare, Jr. | 424/400 |
| 5,632,767 A | 5/1997 | Sinofsky | 607/89 |
| 5,635,482 A | 6/1997 | Bhatnagar | 514/14 |
| 5,643,253 A | 7/1997 | Baxter et al. | 606/17 |
| 5,643,257 A | 7/1997 | Cohen et al. | 606/48 |
| 5,649,924 A | 7/1997 | Everett et al. | 606/15 |
| 5,658,282 A | 8/1997 | Daw et al. | 606/49 |
| 5,785,705 A | 7/1998 | Baker | 606/32 |
| 5,800,529 A | 9/1998 | Brauker et al. | 623/11 |
| 5,954,715 A * | 9/1999 | Harrington et al. | 606/28 |
| 5,979,446 A | 11/1999 | Loy | 128/830 |
| 6,145,505 A * | 11/2000 | Nikolchev et al. | 128/830 |
| 6,309,384 B1 * | 10/2001 | Harrington et al. | 606/28 |
| 6,401,719 B1 * | 6/2002 | Farley et al. | 128/898 |

OTHER PUBLICATIONS

Tibbs, Wound Healing Following Radiation Therapy: A Review, 42 Radiology and Oncology 99–106 (1997).

Brumsted, Attempted Transcervical Occlusion Of The Fallopian Tube With The ND: Yag Laser, 77 Obstetrics And Gynecology 327–28 (Feb. 1991).

Thompson, Vessel Occlusion With Transcatheter Electrocoagulation: Initial Clinical Experience, 133 Radiology 335–340 (Nov. 1979).

Phillips, Experimental Closure Of Arteriovenous Fistula By Transcatheter Electrocoagulation, 115 Radiology 319–21 (May 1975).

Neuwirth, Update On Transcervical Sterilization, 51 International Journal Of Gynecology & Obstetrics, Suppl. 1, S23–28 (1995).

Quinones Guerror, Tubal Electrocauterization Under Hysteroscopic Control, 7 Contraception 195–201 (Mar. 1973).

Quinones, Hysteroscopic Sterilization, 14 International Journal Of Gynecology & Obstetrics 27–34 (1976).

* cited by examiner

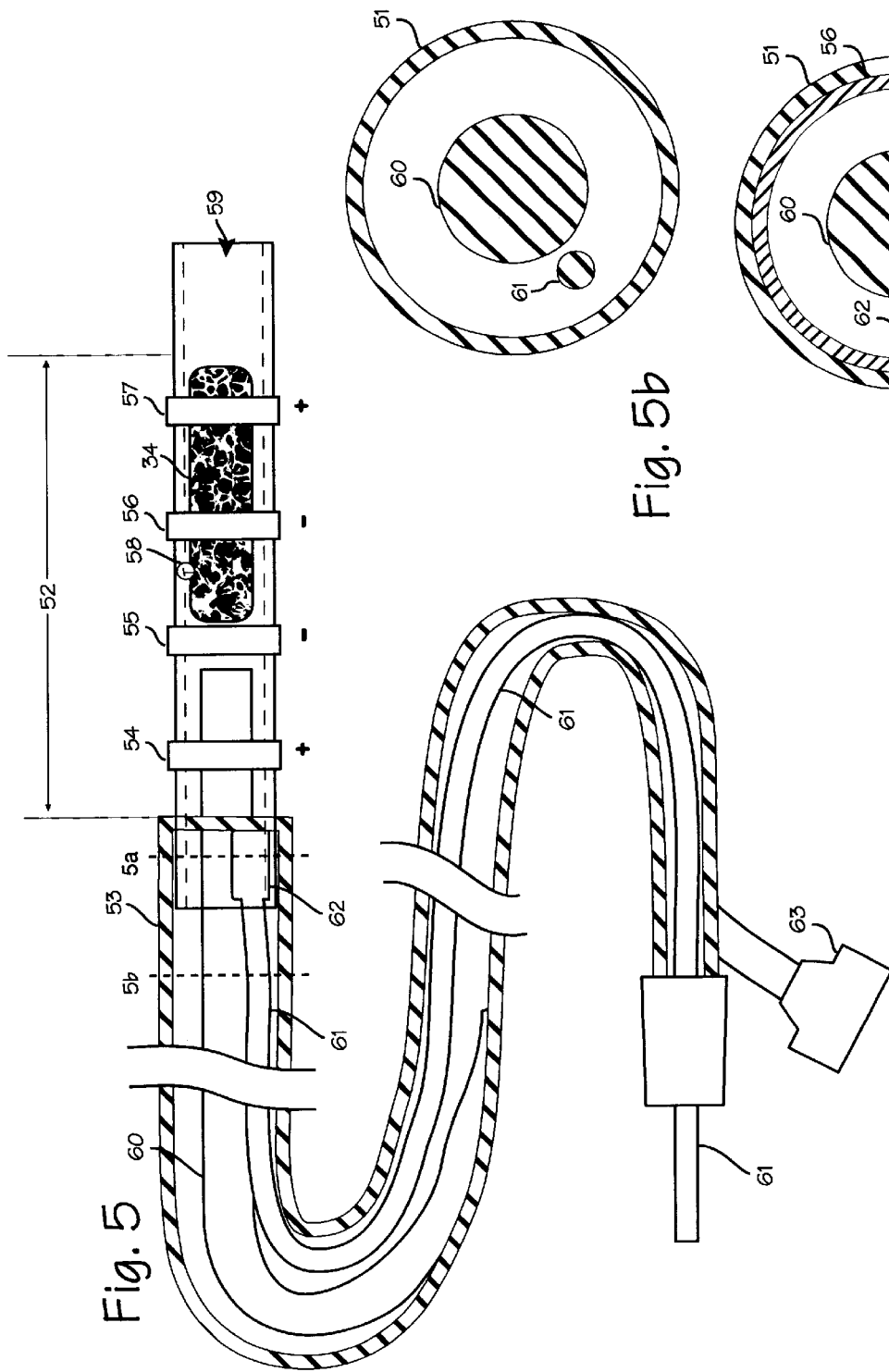

METHOD AND APPARATUS FOR TUBAL OCCLUSION

This application is a continuation of U.S. application Ser. No. 09/241,790 filed Feb. 1, 1999, now U.S. Pat. No. 6,309,384.

FIELD OF THE INVENTIONS

The present invention relates to an apparatus and method for permanently closing body vessels such as the utero-tubal junction, uterine isthmus, and fallopian tubes. In particular, this invention is directed to a relatively simple surgical procedure for sterilizing human females which may be performed in the physician's office.

BACKGROUND OF THE INVENTIONS

It is often desired or necessary for medical reasons to permanently close the fallopian tubes of women. The procedures currently proposed for occluding the fallopian tubes to effect sterilization include surgical ligation, occlusion by insertion of a foreign body, and occlusion by scarring in response to severe wounding.

One method for sterilization in females is surgical tubal ligation, a procedure in which the fallopian tubes are tied and cut, or clamped or fused with instruments passed into the pelvic cavity through an incision made through the wall of the abdomen. When done endoscopically, the pelvic cavity must be pneumatically inflated using an inert gas. Tubal ligation done with a laparotomy requires a surgical incision in the abdomen between 6 and 12 centimeters long done under general anesthesia. Currently, when the fallopian tubes are clamped or fused from the outside of the tubes, they must be clamped or fused at two or three different points in order to ensure that the tubes remain closed.

Various wounding techniques have been proposed. Cohen, et al, *Method for Tubal Electroligation*, U.S. Pat. No. 5,556,396 (Sep. 17, 1996) discloses a method for tubal ligation by providing an electrically energizable electrode to a fallopian tube. The electrode is advanced into the fallopian tube and energized to thermally damage the fallopian tube, thereby causing enough scarring of the fallopian tube to permanently occlude it. In another technique, a sclerosing agent (quinacrine) is injected into the uterus and fallopian tubes to create a permanent closure of the fallopian tubes.

Various plugs have been proposed for occlusion of the fallopian tubes or the utero-tubal junction. One technique involves transcervically injecting a curable elastomeric composition such as silicone into the fallopian tubes in an amount sufficient to fill the portion of the oviduct adjacent the uterus. The elastomeric composition is allowed to solidify to thereby nonsurgically block the tube. Erb, *Method and Apparatus for No-Surgical, Reversible Sterilization of Females*, U.S. Pat. No. 3,805,767 (Apr. 23, 1974). Others have proposed placement of an occlusive wire or coil within the fallopian tubes to occlude them. Ton, *Endoluminal Coil Delivery System Having A Mechanical Release Mechanism*, U.S. Pat. No. 5,601,600 (Feb. 11, 1997), proposes placement of a Guglielmi detachable coil (typically used for vascular occlusion) deep within the fallopian tube, past the isthmus. The coil must be delivered into the fallopian tubes with a delivery catheter extending from the uterus into the fallopian tubes.

Several references suggest that the fallopian tube should be damaged to the point of scarring to weld the tubes shut or to enhance retention of a plug. For example, Vancaillie, Transuterine Sterilization Apparatus and Method, U.S. Pat. No. 5,095,917 (Mar. 17, 1992) teaches a method of forming scar tissue in the fallopian tube to occlude the fallopian tube, including application of chemical scarring agents (tetracycline hydrochloride) or application of high frequency current to the fallopian tubes. The goal is to cause an immediate inflammatory reaction, including edema, arrival of white blood cells, proliferation of fibroblasts and connective tissue, and arrival of macrophages, and also to cause the subsequent healing process which leads to the formation of scar tissue in the damaged area. Lessen, Surgical Method and Electrode Therefor, U.S. Pat. No. 3,858,586 (Jan. 7, 1975) teaches the scarification of the fallopian tubes with the application of RF energy, without placement of a plug afterward, under the theory that the resulting scarring would be sufficient to seal the fallopian tubes. Both the type of injury used to initiate a lesion in the ostium/isthmus/fallopian tube and the nature of the plug material dictates the type of wound healing response that occurs. If high power is used to create the lesion, the biological response of the body will follow a typical inflammatory response and lead to creation of scar tissue.

If the plug material has an architecture, chemistry and/or pore size (smooth, non-porous materials, for example) that induces a foreign body response to the material, this will encourage the formation of scar tissue and a fibrous capsule which surrounds the plug. The foreign body response consists primarily of fibroblasts attraction to the area (including fibroblast insinuation into the plug material, if possible) and the resultant formation of connective matrix with few vascular structures. The foreign body response has also been described as "scar" formation. The cells that comprise this foreign body response can differentiate into myofibroblasts that are capable of contracting around the material and either cause the material to distort or fracture, or in the fallopian tube, dislodge the implant. The combination of the myofibroblastic contractions, peristalic movement of the tube, tubal contractions, and ciliated epithelium create a combined force capable of expulsing the material from the tube.

If the plug is inserted into a fallopian tube without the concomitant disruption of the epithelial cell lining, expulsion of the plug will usually result. The epithelial lining of the fallopian tube functions to protect the underlying layers from infiltration and infection by foreign substances and infectious agents. In the same way, few cells will traverse the epithelial lining to enter the lumen of the fallopian tube, where the plug resides. Thus, implanting a plug in an intact tube results in little, if any, infiltration unto the plug material. Instead, it is likely that a non-infiltrated large pore plug would become a receptacle for necrotic debris shed within the fallopian tube. This could result in higher contamination and infection of the plug matrix. Additionally, the lack of ingrowth would result in less anchoring of the plug matrix, so the expulsion forces present within the fallopian tube could dislodge and expulse the plug. Thus, retention of an intact epithelial layer is not desired, and the epithelial cell layer must be destroyed or disrupted to eliminate the physical barrier to infiltrating cells. After this has occurred, a porous material can be placed into the denuded area, and a wound healing response can follow. Implanting porous materials into a fallopian tube that has an intact epithelial lining does not allow ingrowth into the material, as part of the epithelial cell lining's function is to act as a physical barrier to infectious agents and cellular infiltrate.

Our prior patent application, Harrington et al, *Method And Apparatus For Tubal Occlusion*, U.S. application Ser. No. 09/063,119, (filed May 20, 1998) (the disclosure of which is incorporated herein by reference) illustrates a method blocking off the fallopian tubes by placing a plug in the ostium or cornu of the uterus leading into the fallopian tubes. An exemplary embodiment discussed in our prior application was the application of heat to damage the tissue of the ostium and place a plug into the ostium which, was secured into the ostium by the inflammation of the ostium caused by the thermal injury. The proposed plug comprised a foamed material which permitted the ingrowth of tissue into the plug.

SUMMARY

The method and devices described below provide for occlusion of the fallopian tubes of a woman. The method involves thermally damaging the lining of the utero-tubal junction with relatively low power energy, followed by placement of a reticulated foam plug. The power applied to the lining of the ostium utero-tubal junction is limited to avoid thermal damage to the deep tissue in the area, yet thoroughly damages the superficial tissue. Placement of the plug having suitable flexibility, architecture and foam pore size into the lightly damaged utero-tubal junction encourages the healing tissue to grow into the plug. The tissue that grows into the plug is vascularized to a normal extent, and appears in cross section as an "organoid" mass. Ingrowth of healthy vascularized tissue into the plug prevents or discourages formation of scar tissue around the plug. This minimizes the likelihood of ejection of the plug, and also minimizes the probability that expected re-growth of epithelial tissue in the damaged portion of the utero-tubal junction will continue to the point where fistulation of the occlusion occurs. In another embodiment, the plug comprises a foam having suitable flexibility, architecture and a relatively small foam pore size that does not encourage vascularized tissue ingrowth. This plug is implanted into the lightly damaged utero-tubal junction and encourages formation of a vascularized capsule around the plug. The presence of this vascularized capsule limits the patient's foreign body response, so that the capsule does not constrict around the plug. No substantial ingrowth occurs, although macrophages will most likely infiltrate the plug.

Also presented is a catheter designed for wounding the epithelial layer of the utero-tubal junction, and a method of using the catheter to form a long yet shallow lesion in the utero-tubal junction.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 5 is a drawing of the device used to deliver RF power and an occluding plug to the utero-tubal junction.

FIGS. 5a and 5b show the cross sections of the device illustrated in FIG. 5.

DETAILED DESCRIPTION OF THE INVENTIONS

Figure 1:
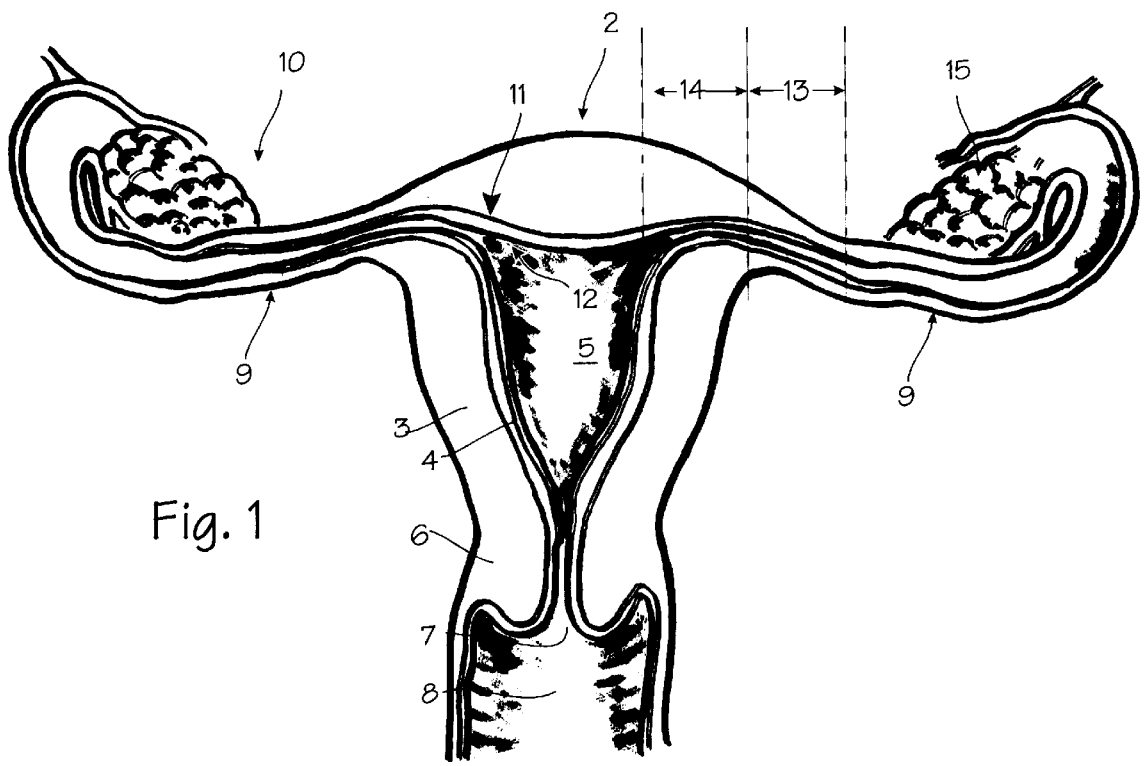
FIG. 1 is a partial view of the female reproductive system.

FIG. 1 shows some of the major elements of the female reproductive system. The uterus 2 is an organ of the female pelvis that has the shape of a pear. It consists of a thick muscular coat, the myometrium 3, a cavity having an inner mucosal lining of variable thickness called the endometrium 4, and a cavity referred to as the uterine cavity 5. The cervix 6 defines the cervical canal 7 which is an inferior opening to the vagina 8. The fallopian tube (or ampulla) 9 is a hollow organ that connects the uterus to the ovary 10. The ovary 15 is the organ that produces one or more eggs during every cycle of a woman's reproductive life. In the human female reproductive system, there is one uterus, two fallopian tubes and two ovaries (under normal conditions). The site where the fallopian tube and uterus connect is called the utero-tubal junction 11. It is a section of tubular shape of about 10 mm in length. Its inner diameter in the resting position is less than 1 mm, but when gas or liquid is pushed through the uterus and tubes, the diameter of the utero-tubal junction may stretch up to about 2 mm. The utero-tubal junction provides a transition between the uterus and the fallopian tube, and the area of transition from the chamber of the uterus to the lumen of the utero-tubal junction is referred to as the ostium or cornu (marked with item number 12). The area of transition between the ostium and the isthmus 13 of the fallopian tube is referred to as the interstitial portion (marked as item 14). The ostium, utero-tubal junction, interstitial portion, isthmus and fallopian tube are part of a pathway leading from the ovaries to the uterus, and this pathway is sometimes referred to as the uterine tube. For the sake of clarity we introduce the term ovarian pathway to denote the entire passageway through which the ova pass when transiting from the ovaries to the uterine cavity.

Figure 2:
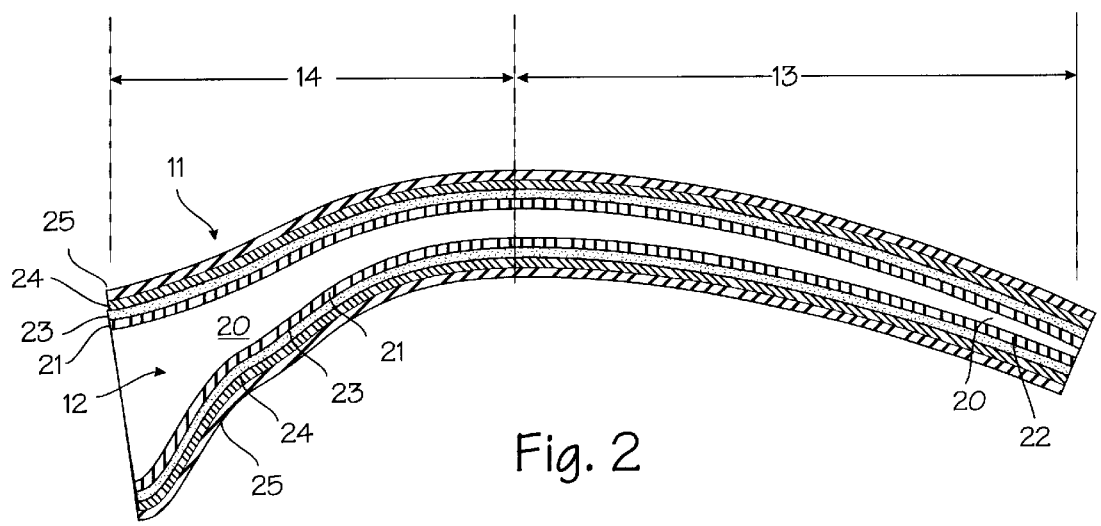
FIG. 2 is a cross section of the utero-tubal junction of the female reproductive system.

FIG. 2 shows the utero-tubal junction 11, including the ostium 12, the isthmus 13, and the interstitial portion 14. The cross section shows the layers of tissue that make up the utero-tubal junction. The lumen 20 passes through the fallopian tube, and this lumen is lined with a layer of mucosal tissue consisting of epithelium 21 and lamina propria 23. Within the fallopian tube, this layer of mucosal tissue is referred to as the endosalpinx, indicated as item 22. The layer of tissue under the epithelial layer is the lamina propria, indicated as item 23. The lamina propria is surrounded by a layer of circular muscle 24 which is surrounded by layer of longitudinal muscle 25. The longitudinal muscle layer may be surrounded with a second layer of circular muscle. The first circular muscle layer 24 typically comprises about 10–14 layers of muscle cells. One aspect of the new treatment method is the extent to which each of these layers is damaged prior to insertion of an occluding plug.

Figure 3:
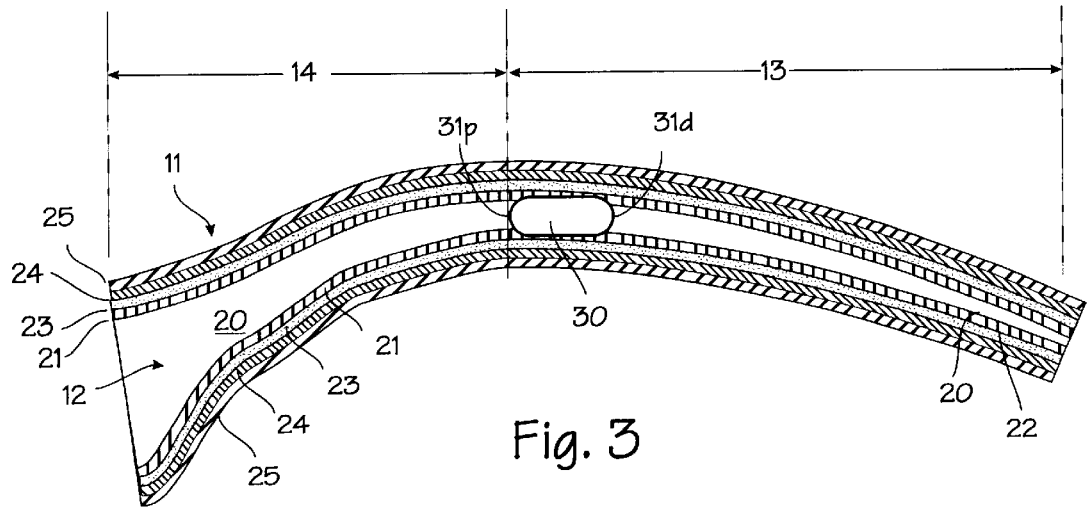
FIGS. 3 and 3a illustrate the prior art method of occluding the fallopian tubes using an occluding plug.

FIG. 3 illustrates an implanted plug 30 placed according to several old methods within the isthmus 13 of the fallopian tube. (Plugs have also been proposed for implantation deep within the fallopian tubes, and in the ostium 12. Sinnreich, Fallopian Tube Obturating Device, U.S. Pat. No. 3,918,431 (Nov. 11, 1975) shows an ostial plug for temporary female sterilization.) The epithelial layer 21 is left intact, and is continuous over the lumen of the ostium/isthmus/fallopian tube in the area occluded by the plug. Some have suggested that the epithelial layer 21 and/or endosalpinx 22 will grow over the distal and proximal faces 31d and 31p (the longitudinal faces) of the plug. In time, the epithelial layer will recanalize the tube and form scar tissue over the plug, resulting in fistula formation around the plug in a number of treated patients. Zeluff, U.S. Pat. No. 4,606,336 suggests use of a foam ring over (not in the lumen of) the ostium, which depends on fibroblast ingrowth into the ring to seal it to the ostium. However, this device is likely to be subject to the uterine foreign body response, leading to abnormal uterine bleeding, increased myometrial and tubal contractions and premature expulsion.

Figure 3A:
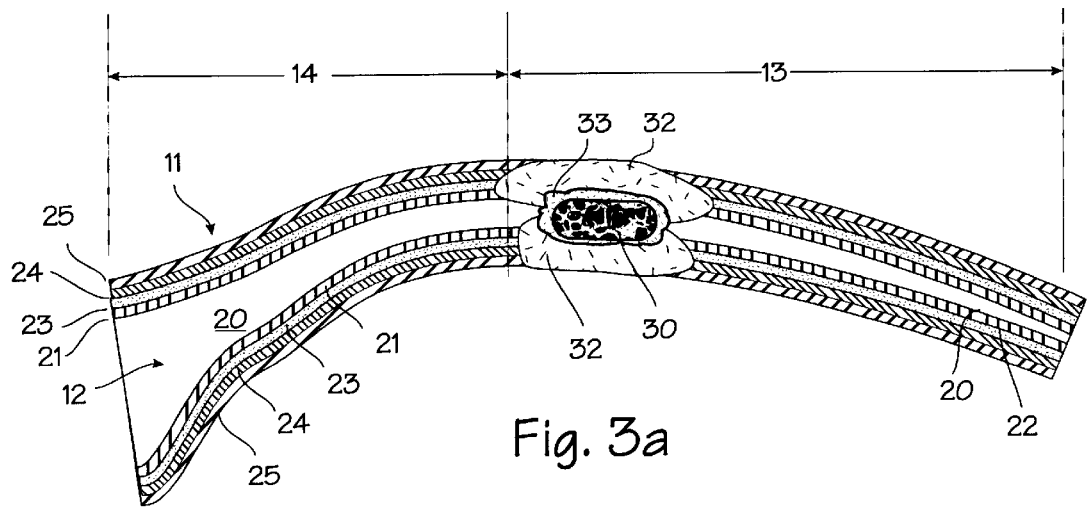

FIG. 3a illustrates the damage in each layer of the fallopian tube which occurs when using methods of the prior art which suggest ablation of the fallopian tubes followed by placement of a plug (the prior art methods do not suggest ablation at the utero-tubal junction). Where RF power has been used, the power is applied in amounts sufficient to damage the entire thickness of the fallopian tube, including the circular muscle layer 24 and longitudinal muscle layer 25. This leads to a "standard foreign body response," which is a term understood among scientists to include inflammation, encapsulation and eventual scar formation. The scar tissue 32 will form in the wounded tissue (resulting in a fundamental change in the tubal architecture), and may also form within the plug if ingrowth is possible. Where a plug is left in the fallopian tube, an avascular fibrotic capsule 33 may form around the plug to protect the host from the plug. Thus, the plug is eventually surrounded by scar tissue and a fibrotic capsule as indicated in FIG. 3a. The biological process of the foreign body response will then operate to expel the plug. The body may also tend to develop epithelium/endosalpinx cells in place of the scar tissue, thereby creating a fistula around the plug, which could result in sperm passage and ova fertilization. The fertilized egg may not be able to locomote through the fistula into the uterus, which would then trap the egg in the tube resulting in an ectopic pregnancy.

Figure 4:
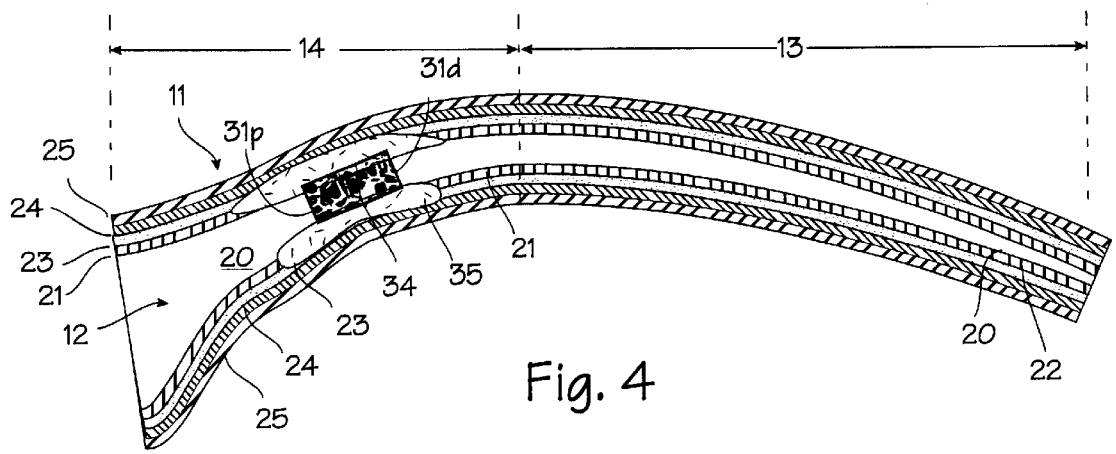
FIGS. 4 and 4a are cross sections of the utero-tubal junction of the female reproductive system with an organoid plug in place.

FIG. 4 illustrates the desired degree of damage in each layer of the utero-tubal junction, and the desired interaction between the tissue and the foam plug which is inserted to generate an occlusion of the fallopian tube. The foam plug 34 is inserted into the target site for occlusion, which in this illustration is the utero-tubal junction. The plug is put in place after the target site has been treated with the application of thermal energy. The thermal energy is delivered at levels well below the level required to cause a severe burn (and the concomitant severe inflammatory response), but sufficient to cause thermal necrosis of the epithelial layer 21 and the lamina propria 23. The area of thermal death (necrosis) is indicated as item 35, and extends for a length of approximately 4 to 10 millimeters along the pathway. Damage to the circular muscle layer 24 is acceptable, but damage to the longitudinal muscle layer 25 is undesirable. This leads to minimal collapse of the utero-tubal junction about the plug. The body responds with normal "wound healing response." The term "wound healing response" is a term understood in the art to include biological activities including: (1) arrival of leukocytes, neutrophils, monocytes, and their transformation into macrophages and aggregation into giant cells, and arrival of fibroblast cells, (collectively referred to as inflammatory cells), and (2) the creation of an extracellular matrix and deposition of proteins, and (3) the formation of granulation and connective tissue at the wound site.

The wound healing response may continue to completion in the surrounding intact pathway, and will further entail reorganization of the granulation tissue into specialized and functional tissue corresponding to the original injured tissue (matching the architecture of the original tissue), and the formation of scar tissue (different from the tissue's original architecture). The tissue response immediately surrounding the plug depends on the composition, pore size and architecture of the plug. For smooth plugs, the response will occur as discussed above in relation to FIGS. 3 and 3a. For the plugs described below, the short term and long-term condition of the tissue immediately surrounding the plug and/or in-growing within the plug depends on the pore size and architecture of the plug. Where the pore size is large relative to the cell size, in the range of 40–200 micron, and of a specific architecture, the body will heal by forming a vascularized tissue within the pores of the foam. Inflammatory cells will enter the foam pores, attract other cells, form extracellular matrix and connective tissue, and form into a collection of tissue referred to as granulation tissue within the pores of the foam. Subsequent healing includes in-growth of vascular structures such as arterioles, capillaries and lymphatic vessels into the connective tissue residing within the pores of the foam. Because of the unique architecture and pore size of the foam, the granulation tissue will remain as granulation tissue indefinitely. Thus the large pore plug, in its final form within the body, will comprise numerous filaments of the foam superstructure which form a network of communicating pores, with granulation tissue occupying the pores. The plug will also comprise numerous blood vessels formed within the granulation tissue, so that the tissue interspersed with the original plug material may be described as vascularized organic tissue. The vascularized tissue is vascularized to the same extent as is typical of other natural organs within the body.

Where the plug pore size is small compared to cell size, in the range of 1–20 microns, vascularized granulation tissue will not form in the plug interstices. Subsequent healing includes formation of a highly vascularized foreign body capsule and intrusion of some macrophages into the plug pores, without intrusion of other cells or tissue associated with the later stages of healing (such as extracellular matrix, granulation tissue and blood vessels). Instead, the body will form a vascularized capsule with blood vessels closely approaching the plug, lying adjacent and within about 10 um of the foam. This may be referred to as an altered foreign body response.

Figure 4A:
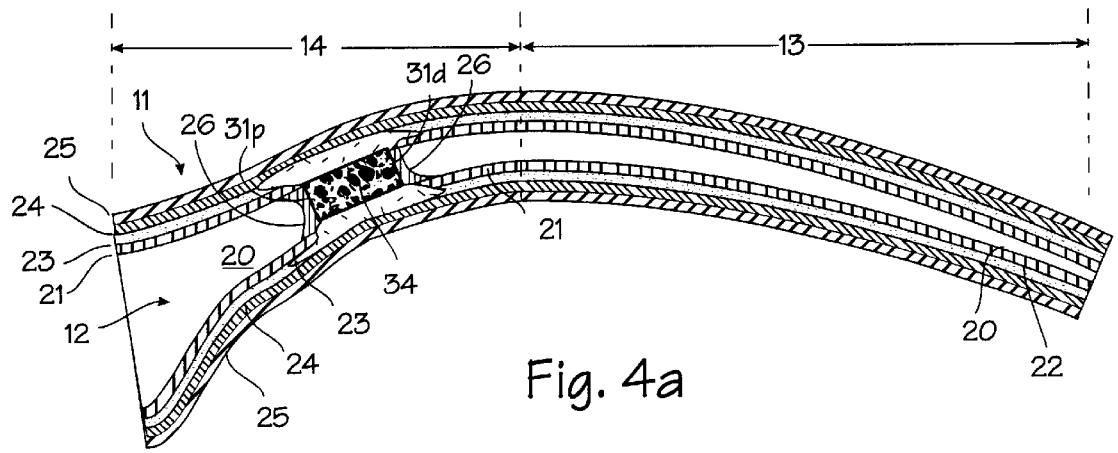
Figure 4B:
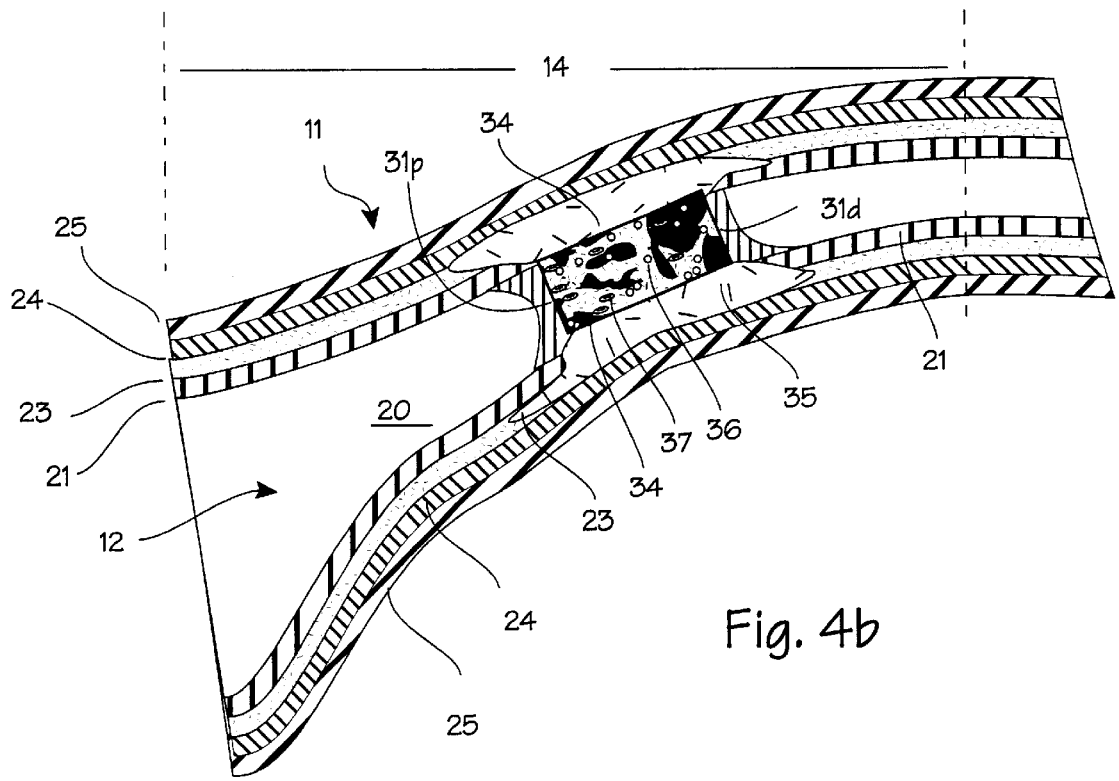
FIGS. 4b and 4c illustrate the boundary response of wounded tissue with organoid plugs in place.
Figure 4C:
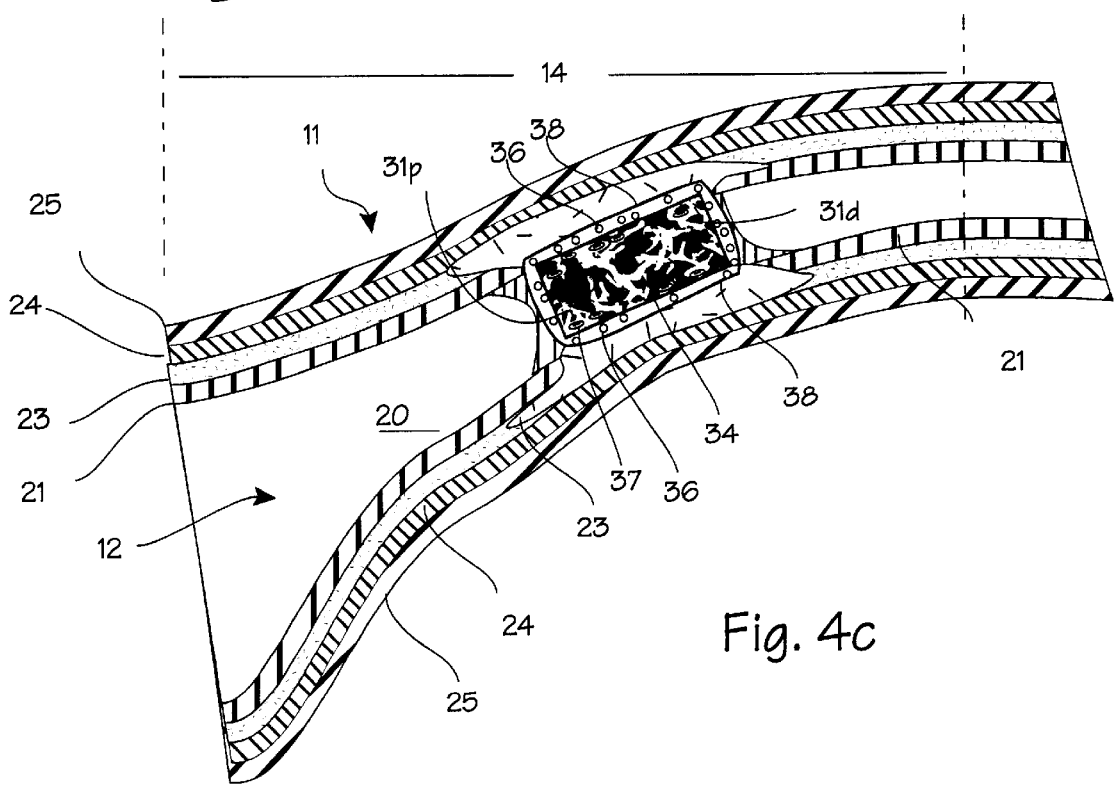

FIG. 4a illustrates the condition of the plug and ovarian pathway after the wound healing process has proceeded to the extent permitted by the continued presence of the plug. The several layers of the target site of the pathway have healed to form healing granulation tissue around the plug and throughout the wounded pathway. Placement of the plug directly against the wounded inner surface of the pathway has encouraged this tissue to surround the plug, and prevented epithelium from forming around the longitudinal surfaces of the plug. Epithelium 26 has grown to cover the distal and proximal faces of the plug to form distal and proximal layers of tissue over the plug. The unwounded longitudinal muscle layer and remaining circular muscle layer remain in the pre-wound condition. After a period of time, a network of new blood vessels organizes within the granulation tissue, and a matrix of connective tissue forms within the granulation tissue. FIG. 4b illustrates the condition of the large pore plug and ovarian pathway after the wound healing process has proceeded to the extent permitted by the continued presence of the plug. The several layers of the target site of the pathway have healed to form healing granulation tissue around the plug and throughout the wounded pathway. Placement of the plug directly against the wounded inner surface of the pathway after wounding has encouraged this tissue to surround the plug, and encouraged healing tissue penetration into the plug (and thus inhibited epithelium from forming around the longitudinal surfaces of the plug). Numerous blood vessels 36 have entered or formed within the large pores. The prior entry of wound healing tissue, including numerous macrophages 37, has inhibited formulation of a fibrous capsule around the plug and epithelial intrusion between the plug and the wounded portion of the ovarian pathway. The body appears to recognize the plug as an organ, and foregoes additional wound healing and foreign body reactions. FIG. 4c illustrates the condition of the small pore plug and ovarian pathway after the wound healing process has proceeded to the extent permitted by the continued presence of the plug. The several layers of the target site of the pathway have healed to form healing granulation tissue around the plug and throughout the wounded pathway. Placement of the plug directly against the wounded inner surface of the pathway after wounding has encouraged this tissue to surround the plug, and prevented epithelium from forming around the longitudinal surfaces of the plug. Scattered macrophages 37 have entered the small pores, and a vascularized altered foreign body capsule 38 has formed around the plug. The vascularized foreign body capsule includes numerous blood vessels, and further progress of the foreign body response is inhibited. Epithelium has grown to cover the distal and proximal faces of the plug to form distal and proximal layers of tissue over the plug.

Thus, depending on the pore size of the plug foam, the plug may be infiltrated with vascularized granulation tissue (for plugs with large pore sizes in the range of 40–200 microns) or infiltrated with scattered macrophages and surrounded with a vascularized capsule of connective tissue (for plugs with small pore sizes in the range of 1–20 microns). In either case, the growth of epithelium between the plug and the wounded portion of the ovarian pathway is inhibited, and the formation of a foreign body avascular fibrous capsule is inhibited by displacement of that structure in favor of other wound healing structures.

The plug is preferably made of a material with a pore size, chemistry and architecture that actually facilitates cellular ingrowth into the material (large pore plugs) or that allow macrophage infiltration but inhibit cellular ingrowth (small pore plugs). Regarding the large pore plugs, the nature of the desired ingrowth is vastly different from the standard foreign body reaction. The primary difference is a type of ingrowth that consists of a variety of blood vessels, connective matrix and cells, macrophages, and other cells. Regarding the small pore plugs, the nature of the foreign body capsule is altered to include numerous blood vessels. These structures can be described as "organoid," as they exist as an integral part of the organ. Two types of materials that we are investigating have displayed this organoid appearance after healing, those materials with a specified architecture and pore size of between 40–200 microns, and those materials that have specific architectures and are microporous (1–20 microns). The wound healing growth would be classified histologically for the small pore materials as resembling the tissue of an "altered foreign body response", and for the larger pore materials, as approaching the look and content of the "dermis".

The plug may be made of ePTFE (also referred to as expanded Teflon or expanded polytetraflouroethylene), porous silicone, acrylic copolymer, cellulose acetate, polyethylene and high density polyethylene (HDPE), PE, polyester, and sintered, micro-knurled, or molded titanium and platinum. Textured polyamides or polyimides, hydroxyapitite, and hydrogels are also potential suitable materials. Preferably, these materials are formed into a plug (a sphere, cylinder or other occluding mass) of foamed material. The preferable pore sizes of the foam fall into the two distinct ranges mentioned above, namely 1–20 micron pore size and 40–200 micron pore size (40–120 microns is even better). The foam is preferably formed as a reticulated foam, meaning that the pores communicate with other pores, rather than existing as discrete and isolated voids within the material. The plug may have a solid core surrounded by foam or a porous material having a reticulated network of pores.

Silicone foam is readily formed into foam plugs with the procedure set forth in Seare, *Method of Making A Porous Device*, U.S. Pat. No. 5,605,693 (Feb. 25, 1997). Uncured silicone (MED 4860 grade supplied by Nusil Technology Corp is suitable) is injected into a form packed with granules, and slowly fills the voids between all the granules. The silicone is cured and the particles are dissolved in a suitable solvent (water, where sugar or salt is used) to form the reticulated foam plug. The foam plug has a durometer value between 20–100 Shore A, preferably about 60 Shore A.

Figure 6:
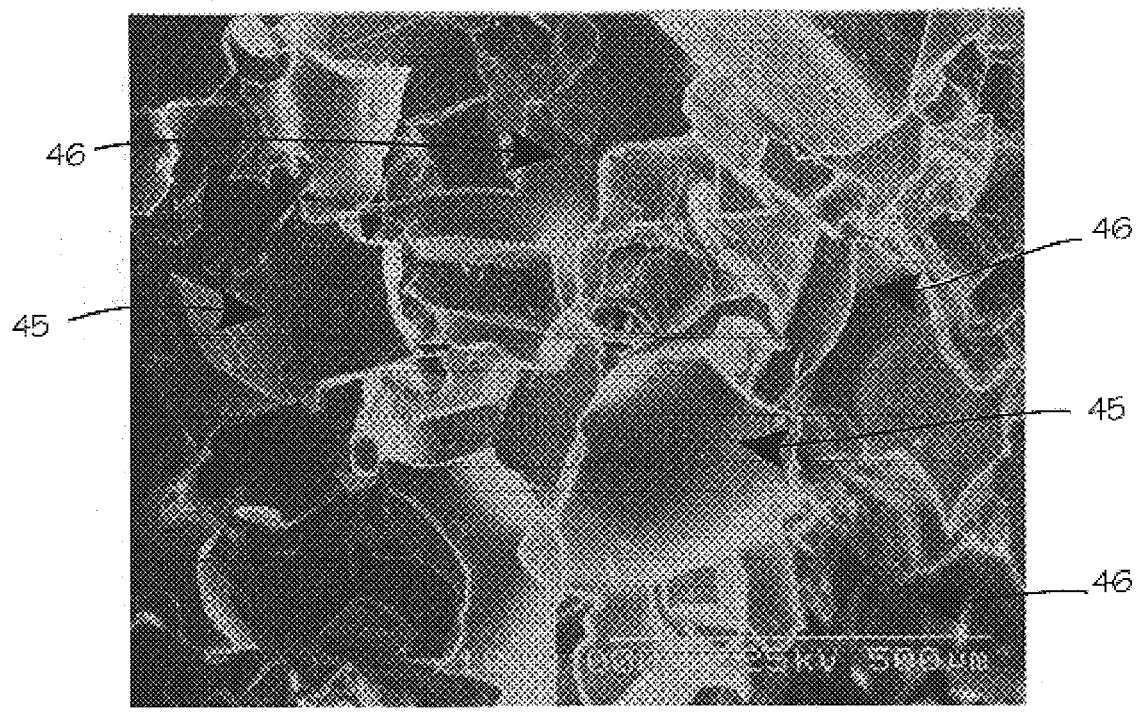
FIGS. 6 and 6a are microscopic views of the plug material used in the sterilization procedure.
Figure 6A:
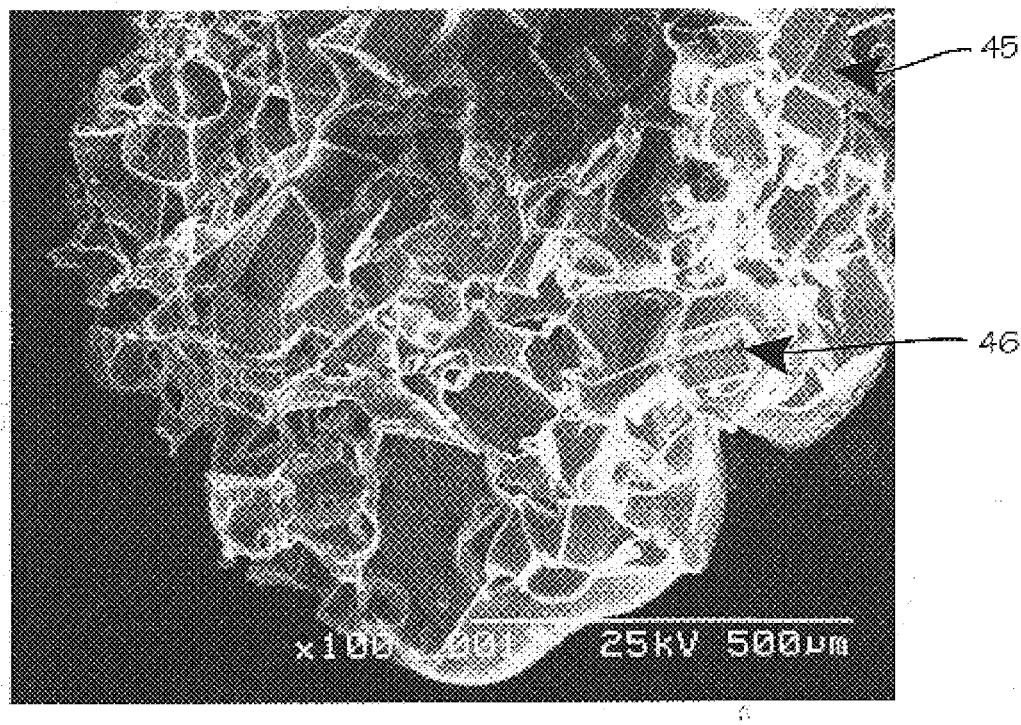

FIGS. 6 and 6a illustrate the two examples of the large pore foam plug. The foam is a matrix of interlocking angular blocks of silicone 45 (only a few are called out with the item number) which are formed together to create a network of communicating pores 46 with sizes corresponding to the size of the granules that were used to make the negative. The pores communicate with surrounding pores to form a reticulated or networked foam. The pore size of the large foam pore illustrated in FIGS. 6 and 6a are in the range of 40–200 microns (mu), the pore size of the foam in FIG. 6a being smaller than the pore size of FIG. 6. The structure of the small pore foam appears essentially the same as FIG. 6, except that the pore sizes is in the range of 1–20 microns.

Figure 7:
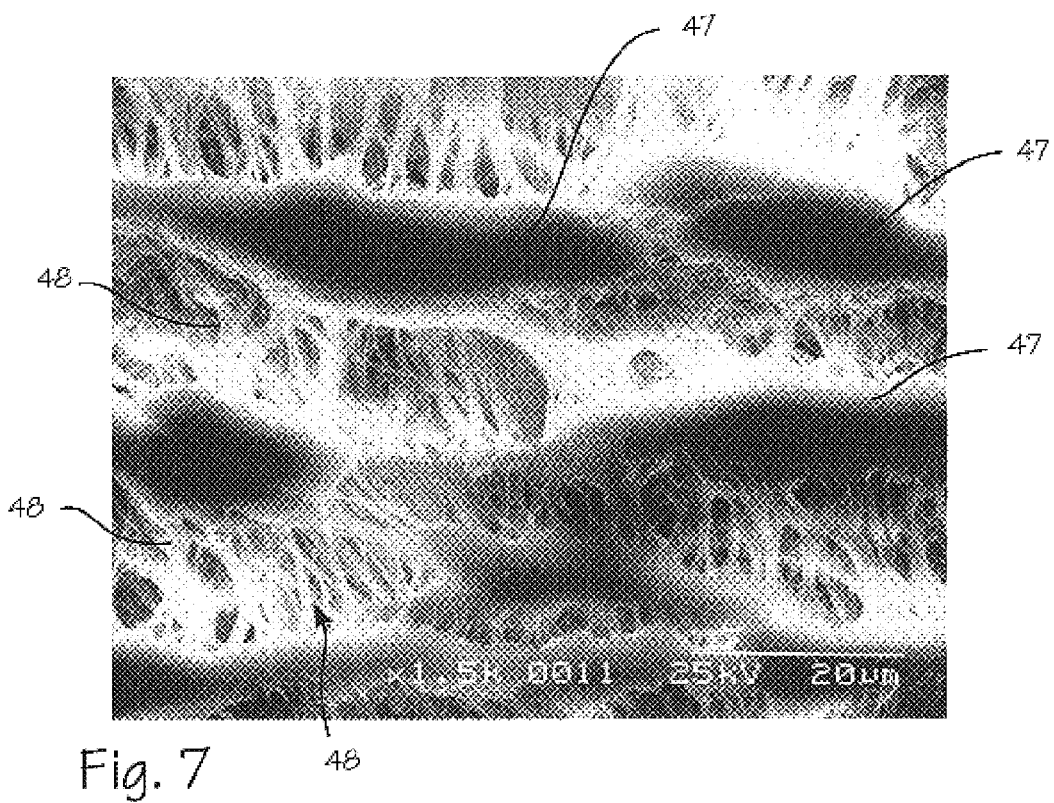
FIGS. 7 and 8 are microscopic views of plug material used in the sterilization procedure.

The plug may be fabricated from expanded polytetraflouroethylene, commonly referred to as ePTFE, with the processes used for forming ePTFE generally. Starting with a PTFE rod, the rod is stretched to expand the PTFE to form the system of nodes and fibrils characteristic of ePTFE. Pore size (commonly referring to the distance between the nodes) and the number and size of fibrils connecting the nodes is controlled by stretching the PTFE rods at controlled rates and temperatures. (The plugs may also be fabricated from sheets of PTFE which are stretched to the degree necessary to create the desired porosity, then cut to shape. The plugs may also be formed of very thin sheets of ePTFE which are used to coat or wrap a solid rod of PTFE.) The process results in a material illustrated in FIG. 7 having microstructure characterized by elongate nodes 47 interconnected by fibrils 48 running between the nodes and extending generally perpendicular to the long dimension of the nodes. The pore size, as measured between the nodes, is in the range of 40 to 200 microns for large pore foam and 1 to 10 microns for small pore foam.

Figure 8:
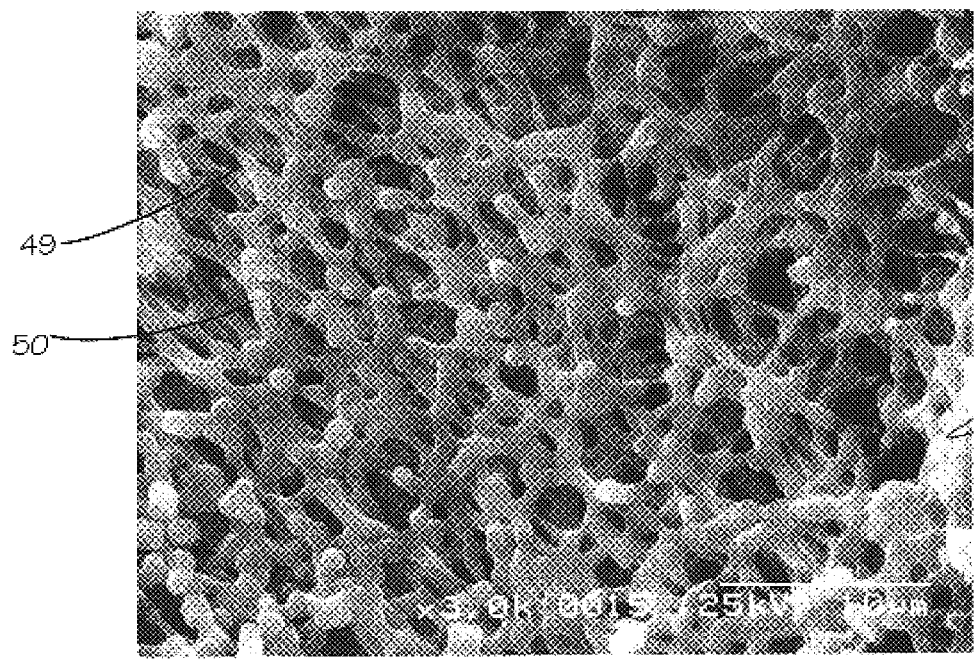

The plug may also be formed of acrylic copolymer (such as tetrafluoroethylene and hexafluoropropylene), as illustrated in FIG. 8. The acrylic copolymer is formed as a mass of interlocking fibers 49, which on the outer surface of the foam become outwardly extending rods 50. The pore size, as measured by the distance between the rods is preferably in the range of 1 to 10 microns.

The delivery catheter developed for delivery of the plugs and to apply the desired wounding system is illustrated in FIG. 5. FIG. 5 illustrates an embodiment in which the wounding energy source is RF energy. The catheter includes a catheter body 51 with a wounding segment 52 comprising a short tubular extension slidably mounted within the distal tip 53 of the catheter. The distal tip of the catheter body extends over the proximal end of the tubular extension for a short length of 2–25 mm, which is sufficient to firmly hold the tubular extension during use. Four electrodes 54, 55, 56 and 57 are aligned along the outer surface of the wounding segment. One or more temperature sensors 58 are mounted on the wounding segment (a single temperature sensor may be mounted in the center of wounding segment, between the ground electrodes). The distal tip and wounding segment are about 55 mil in outer diameter. The wounding segment in the RF embodiment is about 6 to 8 mm long, and the electrodes are ring electrodes which are about 0.037 to 0.050 inches wide (measured along of the longitudinal axis of the catheter) and wrap around the catheter. One or more foam plugs 34 are stored within the catheter body, and are shown housed within the wounding segment. By arranging the electrodes with the energized or hot electrodes 54 and 57 on the distal and proximal ends of the wounding segment, with the ground electrodes 55 and 56 situated between the hot electrodes, a long and shallow lesion may be produced in the ovarian pathway when the electrodes are energized appropriately. The converse pattern of ground electrodes located on the distal and proximal ends of the wounding segment with energized electrodes located between the ground electrodes may also be used to create the desired long and shallow lesion.

The plugs may be compressed to fit into the lumen 59 in the wounding segment of the catheter. A holding rod 60 is disposed within the catheter body 51, fixed longitudinally within the catheter body at any point distal to the wounding segment (it may be secured by gluing or heat sealing a proximal segment of the holding rod to the inner wall of the catheter body) which permits adequate pullback of the wounding segment to release the plug. A pullwire 61 is secured to the proximal end of the wounding segment by attachment of the boss 62 on the distal end of the pullwire. The pullwire extends distally from the wounding segment to the proximal end of the catheter body. FIG. 5a shows the cross section of the device along section 5a, more clearly illustrating the relative positions of the pullwire boss 62 fixed to the inner wall of the wounding segment 52, which itself is slidably disposed within the distal tip 53 of the catheter body 51, and also slidably disposed around the holding rod 60. FIG. 5b shows the cross section of the device along cross section 5b, more clearly illustrating the position of the holding rod 60 within the catheter body 51. The pullwire 61 can be manipulated by hand from the proximal end of the catheter to pull the wounding segment proximally within the catheter body. The holding rod 60 maintains the plug (or plugs) in position within the ovarian pathway while the wounding segment is pulled proximally, thereby ejecting the plugs from the distal tip of the catheter without moving them relative to the wounded segment of the ovarian pathway after initial positioning (and also without moving the catheter body relative to the patient). Electrical wires which supply RF power to the electrodes may run the through the lumen of the catheter body alongside the pullwire or they may be housed within the catheter body, and an electrical connector 63 is supplied on the proximal end of the catheter to connect the wires in the catheter to the RF power supply. The electrical wires may also be incorporated into the pullwire, with the electrical connections to the RF power supply being disposed on the proximal end of the pullwire. Other wounding mechanisms may be employed, including resistive heating elements, direct laser irradiation, laser heated elements, microwave, ultrasound, piezo-electric abrasion, hypothermia, cryothermia, chemical ablation, and mechanical and physical abrasion.

In use, the catheter is inserted into the uterus transcervally, and the distal tip of the catheter is navigated into the fallopian tubes, until the wounding segment is stationed at the desired point along the ovarian pathway (the utero-tubal junction is our preferred location for the wound and the plug placement). Surgeons may view the placement with an endoscope or hysteroscope, and/or placement within the pathway can be confirmed with fluoroscopy. (Of course, placement of the catheter may be accomplished blindly, using tactile feedback only.) Once the wounding element is in place, the appropriate wound may be created by application of power limited so as destroy the epithelial layer/endosalpinx in the area of plug placement, yet avoid unwanted physiological reactions. The goal is to completely necrose the epithelium/endosalpinx, and to accomplish this goal, the surgeon applies sufficient wounding power to necrose the epithelium/endosalpinx, and the lamina propria, while limiting the wounding power to prevent damage to the longitudinal muscle layer. Damage to the circular muscle layer should be insubstantial, but may be tolerated. After wounding the ovarian pathway, the wounding segment is withdrawn by pulling the pullwire proximally while holding the catheter in place. This ejects the plug without need for relative motion between the plug and the wound after the operator has positioned the catheter for use.

When using RF energy as the wounding mechanism, we have determined that power of 0.1 to 5 watts for about 5 to 60 seconds causes thermal necrosis of the epithelial layer, without damaging the longitudinal muscle layer and without inducing an acute inflammatory response. Preferably, temperature in the tissue is monitored with temperature sensors mounted on the delivery catheter wounding segment, and power is applied to maintain tissue temperature in the range of 40–80° C. for a period of 5 to 60 seconds. Experimentally, we have determined that maintaining temperature of about 70° C. for 7 seconds works well. Also, maintaining temperature in the range of 52–58° C. for 40–60 seconds works well. The heating may also be accomplished in two stages, heating briefly to 70–80° C. (5 to 10 seconds) followed by heating to 40–60° C. for an additional 30 to 60 seconds.

Figure 9:
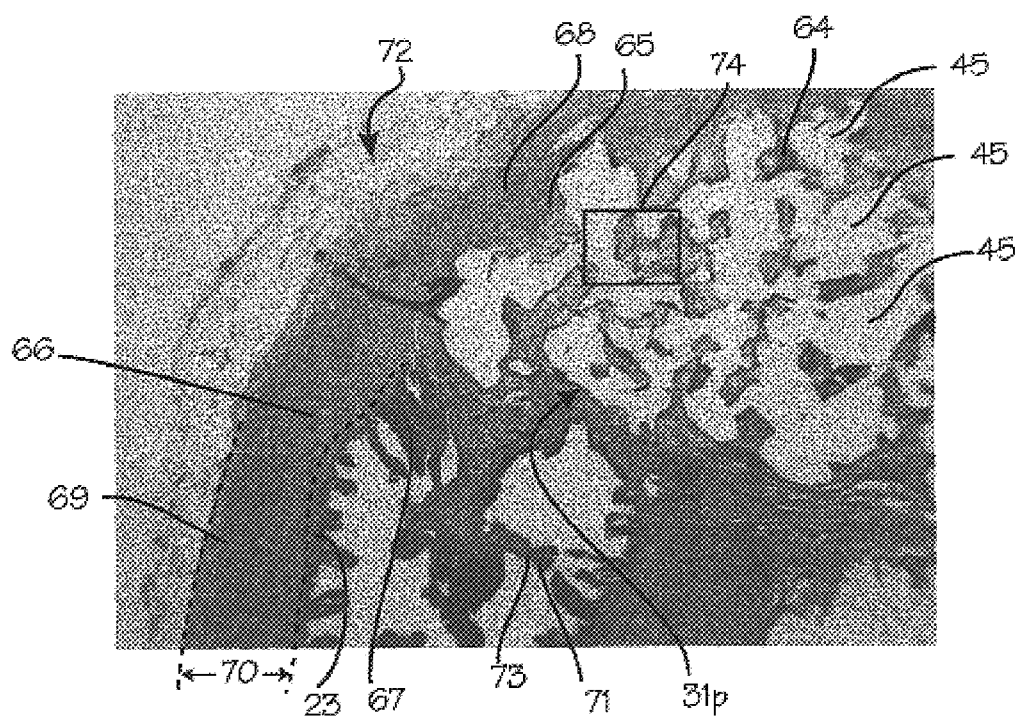
FIGS. 9 and 9a illustrate the plug composition after placement and partial healing.
Figure 9A:
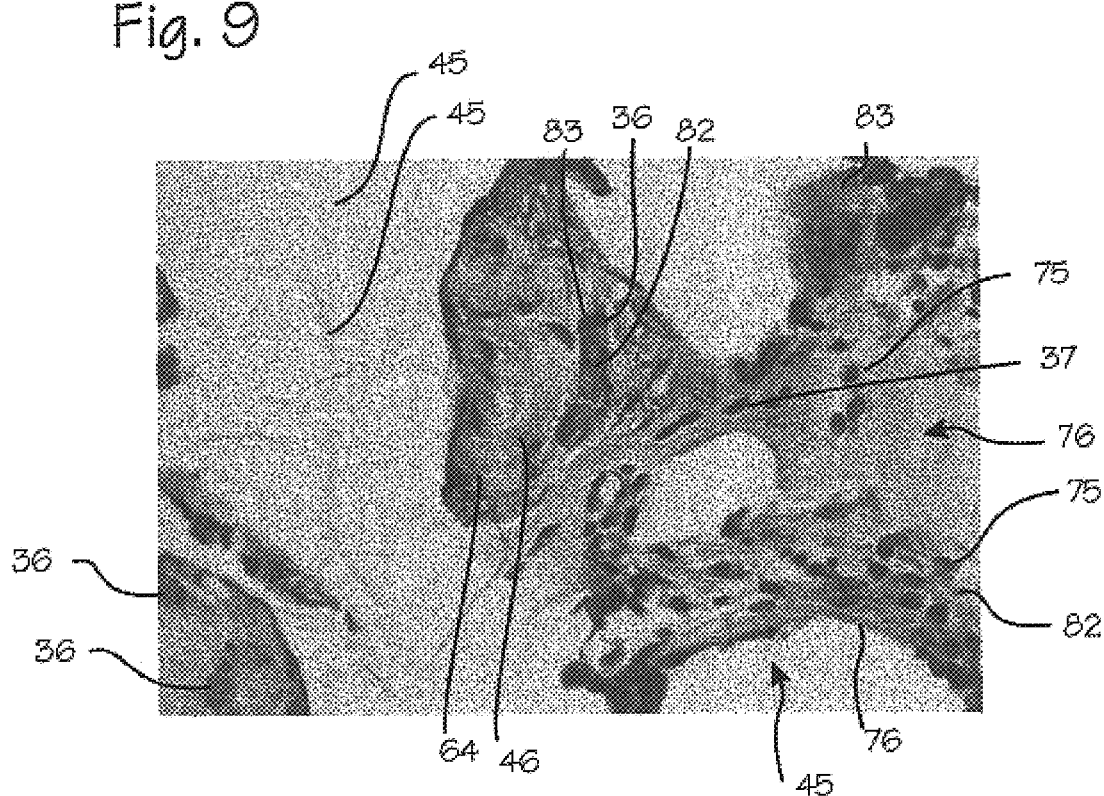

FIGS. 9 and 9a are photographs of an actual implant with the large pore foam. FIGS. 9 shows the cross section of a bending segment of the ovarian pathway, which includes a view of the large pore plug in relation to the surrounding wounded ovarian pathway tissue, several weeks after implantation as well as an uninjured portion of the ovarian pathway. The silicone foam basis of the plug in this illustration is the whitish gray irregular mass indicated as item 45. The ingrown tissue 64, surrounding wounded ovarian pathway tissue 65 and unwounded ovarian tissue 66 have been dyed to assist in identifying the structures present. The ovarian pathway tissue visible in FIG. 9 includes the injured and healing lamina propria 67, the injured and healing muscle layers 68, and the uninjured longitudinal muscle 69 (the circular and longitudinal layers cannot be readily distinguished in the photograph, and are located in the area indicated by item number indicated 70). The epithelial/endosalpinx layer is not present, having been destroyed by the wounding process (although the epithelial layer 71 is visible in the unwounded tissue 66. Other structures which are visible include serosa 72, the plicae (folds) 73 of the ovarian pathway in the unwounded tissue 66. The details of the wound healing tissue 64 within the plug are visible in the higher magnification view of FIG. 9a, which is an enlargement of the area 74 of FIG. 9. Individual granules of silicone 45 are visible in the silicone foam basis 45 Within the pores 46, the wound healing tissue 64 has progressed into the makeup of granulation tissue, and the typical mononuclear cells 75, macrophages 37 and several blood vessels 36 (containing visible endothelial cells 83 in the wall of the blood vessel and visible red blood cells 82 within the lumen of the blood vessel) are visible. Extracellular matrix 76 also fills much of the volume of the pores.

Figure 10:
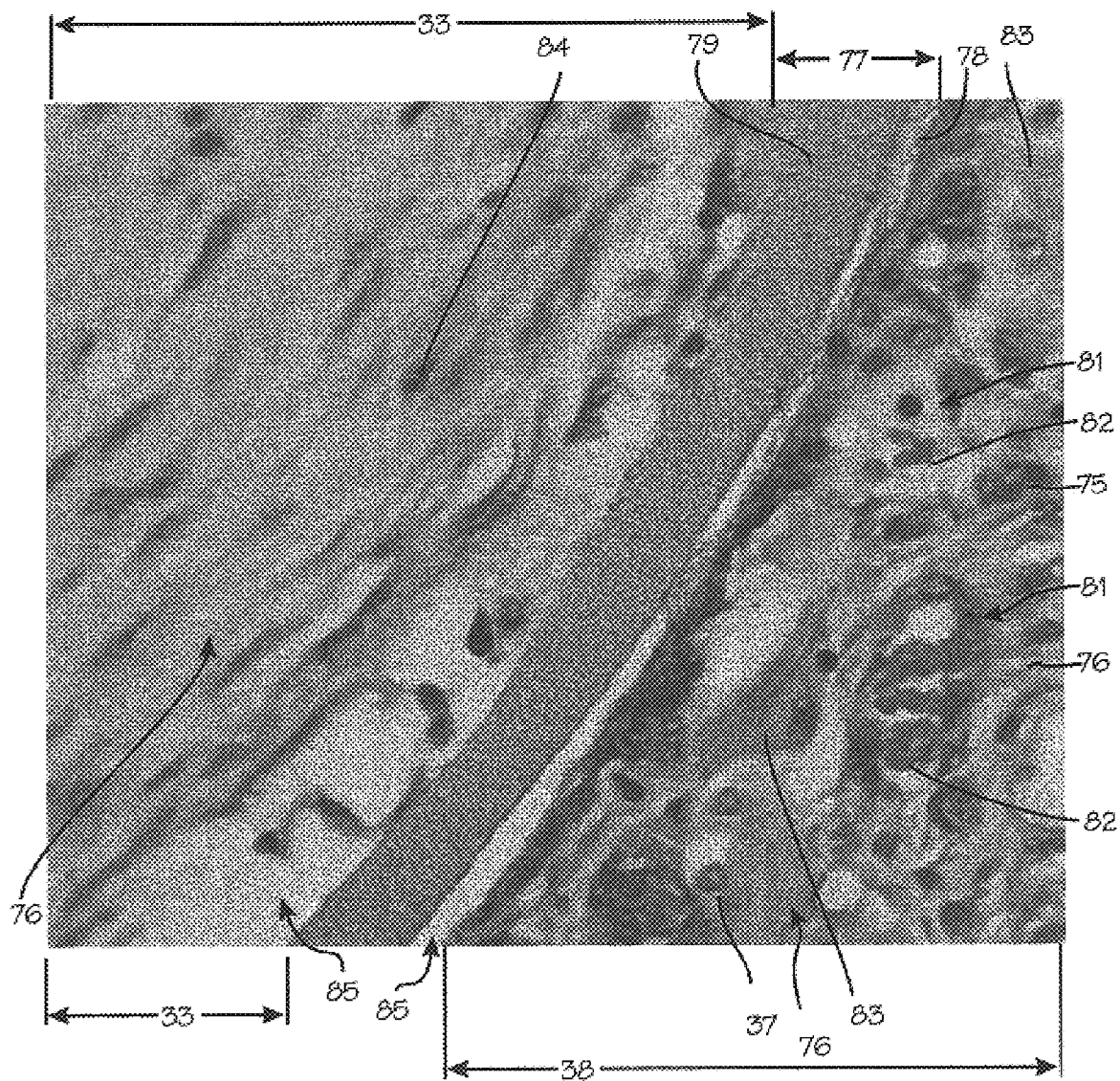
FIG. 10 illustrates the plug composition after placement and partial healing.

Formation of the vascularized fibrotic capsule is illustrated in FIG. 10, which is a photograph of a plug comprising a bilaminar membrane 77 comprising the small pore ePTFE, a smooth membrane ePTFE and the surrounding ovarian pathway tissue. The plug is actually two sided, having a small pore side 78 with 5 micron pore ePTFE on the right, and an essentially smooth side 79 with 0.45 micron pore ePTFE on the left. FIG. 10 shows the cross section of this two sided plug in relation to the surrounding ovarian pathway tissue, several weeks after implantation. In FIG. 10, The healing lamina propria 67 the injured and healing circular muscle layer 68, and the uninjured longitudinal muscle 69 are not visible around the plug in this close up view. On the small pore side of the plug, a vascularized foreign body capsule 38 has developed. The blood vessels 81 formed within the vascularized altered foreign body capsule 38 are seen closely approaching the plug (individual red blood cells 82 can be seen inside the blood vessels). Other structures which are visible include extracellular matrix 76, scattered macrophages 37, mononuclear leukocytes 75 and giant cells 83. On the smooth side of the plug, the avascular fibrotic capsule 33 characteristic of the foreign body response is visible. The avascular fibrotic capsule is composed entirely of extracellular matrix 76 and scattered fibroblast cells 84 throughout the extracellular matrix. No blood vessels have formed in the avascular fibrotic capsule, a clear sign that the smooth side of the plug has been isolated by the foreign body response. (The white spaces 85 are merely separations between various structures created when the tissue surrounding the plug was splayed for histology.)

While the preferred embodiments of the devices and methods have been described in reference to the environment in which they were developed, they are merely illustrative of the principles of the inventions. It is contemplated that additional materials may be developed for use in the inventions described, and that additional means for wounding the ovarian pathway may be developed for use with inventions described. Other embodiments and configurations may be devised without departing from the spirit of the inventions and the scope of the appended claims.

We claim:

1. A method of occluding the ovarian pathway of a female body, wherein the ovarian pathway is lined by an epithelial layer on the inner surface of the ovarian pathway, said method comprising the steps of:
applying a wounding element in the form of a catheter-mounted heating element and a catheter mounted temperature sensor positioned on the catheter in proximity to the heating element to a target segment of the pathway, and operating the wounding element to cause a wound in the segment of the pathway that necroses the epithelial layer;
limiting the severity of the wound created by the wounding element by controlling the heating element to heat the ovarian pathway to a temperature range of 40–80° C. as sensed by the temperature sensor, for a period of at least about 5 seconds;
installing a foam plug comprising a reticulated foam into the wounded segment of the pathway; and
allowing the wounded segment of the pathway to heal with the foam plug installed.

2. A method of occluding the ovarian pathway of a female body, wherein the ovarian pathway is lined by an epithelial layer on the inner surface of the ovarian pathway, said method comprising the steps of:
applying a catheter-mounted RF electrode array to a target segment of the ovarian pathway and operating the catheter-mounted RF electrode array to generate RF energy which causes a wound in the segment of the ovarian pathway that necroses the epithelial layer;
controlling the RF energy applied to the ovarian pathway by maintaining a temperature in the ovarian pathway in the range of approximately 40–80° C. for at least about 5 seconds;
installing a foam plug comprising a reticulated foam into the wounded segment of the pathway; and
allowing the wounded segment of the pathway to heal with the foam plug installed.

3. A method of occluding the ovarian pathway of a female body, wherein the ovarian pathway is lined by an epithelial layer on the inner surface of the ovarian pathway, said method comprising the steps of:
applying a wounding element in the form of a catheter-mounted heating element and a catheter mounted temperature sensor positioned on the catheter in proximity to the heating element to a target segment of the pathway, and operating the wounding element to cause a wound that necroses the epithelial layer in the segment of the pathway;
limiting the severity of the wound created by the wounding element by controlling the heating element to heat the ovarian pathway to a temperature range of approximately 52–58° C. as sensed by the temperature sensor, for a period of at least about 40 seconds;
installing a foam plug comprising a reticulated foam into the wounded segment of the pathway; and
allowing the wounded segment of the pathway to heal with the foam plug installed.

4. A method of occluding the ovarian pathway of a female body, wherein the ovarian pathway is lined by an epithelial layer on the inner surface of the ovarian pathway, said method comprising the steps of:
applying a catheter-mounted RF electrode array to a target segment of the ovarian pathway and operating the catheter-mounted RF electrode array to generate RF energy which causes a wound in the segment of the ovarian pathway that necroses the epithelial layer;
controlling the RF energy applied to the ovarian pathway by maintaining a temperature in the ovarian pathway in the range of 52–58° C. for at least 40 seconds;
installing a foam plug comprising a reticulated foam into the wounded segment of the pathway; and
allowing the wounded segment of the pathway to heal with the foam plug installed.

5. A method of occluding the ovarian pathway of a female body, wherein the ovarian pathway is lined by an epithelial layer on the inner surface of the ovarian pathway, said method comprising the steps of:
applying a wounding element in the form of a catheter-mounted heating element and a catheter mounted temperature sensor positioned in proximity to the heating element to a target segment of the pathway, and operating the wounding element to cause a wound that necroses the epithelial layer in the segment of the pathway;

limiting the severity of the wound created by the wounding element by controlling the heating element to heat the ovarian pathway to a temperature of approximately 70° C. as sensed by the temperature sensor, for a period of at least about 7 seconds;

installing a foam plug comprising a reticulated foam into the wounded segment of the pathway; and allowing the wounded segment of the pathway to heal with the foam plug installed.

6. A method of occluding the ovarian pathway of a female body, wherein the ovarian pathway is lined by an epithelial layer on the inner surface of the ovarian pathway, said method comprising the steps of:

applying a catheter-mounted RF electrode array to a target segment of the ovarian pathway and operating the catheter-mounted RF electrode array to generate RF energy which causes a wound in the segment of the ovarian pathway that necroses the epithelial layer;

controlling the RF energy applied to the ovarian pathway by maintaining a temperature in the ovarian pathway at approximately 70° C. for approximately at least about 7 seconds;

installing a foam plug comprising a reticulated foam into the wounded segment of the pathway; and allowing the wounded segment of the pathway to heal with the foam plug installed.

7. A method of occluding the ovarian pathway of a female body, said method comprising the steps of:

applying a heating element to a target segment of the pathway, and operating the heating element to heat the target segment in the pathway;

limiting the heating of the target segment by controlling the heating element to heat the target segment to a temperature range of 40–80° C. for a period of at least about 5 seconds;

installing a plug into the target segment of the pathway.

8. The method of claim 7 additionally comprising the step of providing the heating element in the form of at least one electrode adapted for application to the ovarian pathway.

9. The method of claim 8 additionally comprising the step of applying RF energy to the target segment through the electrode.

10. The method of claim 7 additionally comprising the step of providing the heating element in the form of at least two electrodes adapted for application to the ovarian pathway, and applying bi-polar RF energy to said electrodes.

11. The method of claim 7 additionally comprising the step of providing the heating element in the form of at least one resistive heating element adapted for application to the ovarian pathway.

12. The method of claim 7 additionally comprising the step of providing the heating element in the form of at least one microwave heating element adapted for application to the ovarian pathway.

13. The method of claim 7 additionally comprising the step of providing the heating element in the form of at least one ultrasound heating element adapted for application to the ovarian pathway.

14. The method of claim 7 additionally comprising the step of providing the heating element in the form of at least one laser heating element adapted for application to the ovarian pathway.

15. The method of claim 7 additionally comprising the step of providing the plug in the form of a reticulated foam plug having pores with pore sizes in the range of 40 to 200 microns.

16. The method of claim 7 additionally comprising the step of providing the plug in the form of a reticulated foam plug having pores with pore sizes in the range of 1 to 20 microns.

17. A method of occluding the ovarian pathway of a female body, wherein the ovarian pathway is lined by an epithelial layer on the inner surface of the ovarian pathway, and wherein the ovarian pathway is further characterized by a lamina propria layer surrounding the epithelial layer, a circular muscle layer surrounding the lamina propria layer and a longitudinal muscle layer surrounding the circular muscle layer, said method comprising the steps of:

applying a wounding element in the form of a catheter-mounted heating element and a catheter mounted temperature sensor positioned on the catheter in proximity to the heating element to a target segment of the pathway, and operating the wounding element to cause a wound in the segment of the pathway that necroses the epithelial layer;

limiting the outward extent of the wound to the circular muscle layer by controlling the heating element to heat the ovarian pathway to a temperature range of 40–80° C. as sensed by the temperature sensor, for a period of at least about 5 seconds;

installing a foam plug comprising a reticulated foam into the wounded segment of the pathway; and allowing the wounded segment of the pathway to heal with the foam plug installed.

18. A method of occluding the ovarian pathway of a female body, wherein the ovarian pathway is lined by an epithelial layer on the inner surface of the ovarian pathway, and wherein the ovarian pathway is further characterized by a lamina propria layer surrounding the epithelial layer, a circular muscle layer surrounding the lamina propria layer and a longitudinal muscle layer surrounding the circular muscle layer, said method comprising the steps of:

applying a catheter-mounted RF electrode array to a target segment of the ovarian pathway and operating the catheter-mounted RF electrode array to generate RF energy which causes a wound in the segment of the ovarian pathway that necroses the epithelial layer;

controlling the RF energy applied to the ovarian pathway to limit the outward extent of the wound to the circular muscle layer by maintaining a temperature in the ovarian pathway in the range of approximately 40–80° C. for at least about 5 seconds;

installing a foam plug comprising a reticulated foam into the wounded segment of the pathway; and allowing the wounded segment of the pathway to heal with the foam plug installed.

19. A method of occluding the ovarian pathway of a female body, wherein the ovarian pathway is lined by an epithelial layer on the inner surface of the ovarian pathway, and wherein the ovarian pathway is further characterized by a lamina propria layer surrounding the epithelial layer, a circular muscle layer surrounding the lamina propria layer and a longitudinal muscle layer surrounding the circular muscle layer, said method comprising the steps of:

applying a wounding element in the form of a catheter-mounted heating element and a catheter mounted temperature sensor positioned on the catheter in proximity to the heating element to a target segment of the pathway, and operating the wounding element to cause a wound that necroses the epithelial layer in the segment of the pathway;

limiting the outward extent of the wound to the circular muscle layer by controlling the heating element to heat the ovarian pathway to a temperature range of approximately 52–58° C. as sensed by the temperature sensor, for a period of at least about 40 seconds;

installing a foam plug comprising a reticulated foam into the wounded segment of the pathway; and allowing the wounded segment of the pathway to heal with the foam plug installed.

20. A method of occluding the ovarian pathway of a female body, wherein the ovarian pathway is lined by an epithelial layer on the inner surface of the ovarian pathway, and wherein the ovarian pathway is further characterized by a lamina propria layer surrounding the epithelial layer, a circular muscle layer surrounding the lamina propria layer and a longitudinal muscle layer surrounding the circular muscle layer, said method comprising the steps of:

applying a catheter-mounted RF electrode array to a target segment of the ovarian pathway and operating the catheter-mounted RF electrode array to generate RF energy which causes a wound in the segment of the ovarian pathway that necroses the epithelial layer;

controlling the RF energy applied to the ovarian pathway to limit the outward extent of the wound to the circular muscle layer by maintaining a temperature in the ovarian pathway in the range of 52–58° C. for at least 40 seconds;

installing a foam plug comprising a reticulated foam into the wounded segment of the pathway; and allowing the wounded segment of the pathway to heal with the foam plug installed.

21. A method of occluding the ovarian pathway of a female body, wherein the ovarian pathway is lined by an epithelial layer on the inner surface of the ovarian pathway, and wherein the ovarian pathway is further characterized by a lamina propria layer surrounding the epithelial layer, a circular muscle layer surrounding the lamina propria layer and a longitudinal muscle layer surrounding the circular muscle layer, said method comprising the steps of:

applying a wounding element in the form of a catheter-mounted heating element and a catheter mounted temperature sensor positioned in proximity to the heating element to a target segment of the pathway, and operating the wounding element to cause a wound that necroses the epithelial layer in the segment of the pathway;

limiting the outward extent of the wound to the circular muscle layer by controlling the heating element to heat the ovarian pathway to a temperature of approximately 70° C. as sensed by the temperature sensor, for a period of at least about 7 seconds;

installing a foam plug comprising a reticulated foam into the wounded segment of the pathway; and allowing the wounded segment of the pathway to heal with the foam plug installed.

22. A method of occluding the ovarian pathway of a female body, wherein the ovarian pathway is lined by an epithelial layer on the inner surface of the ovarian pathway, and wherein the ovarian pathway is further characterized by a lamina propria layer surrounding the epithelial layer, a circular muscle layer surrounding the lamina propria layer and a longitudinal muscle layer surrounding the circular muscle layer, said method comprising the steps of:

applying a catheter-mounted RF electrode array to a target segment of the ovarian pathway and operating the catheter-mounted RF electrode array to generate RF energy which causes a wound in the segment of the ovarian pathway that necroses the epithelial layer;

controlling the RF energy applied to the ovarian pathway to limit the outward extent of the wound to the circular muscle layer by maintaining a temperature in the ovarian pathway at approximately 70° C. for approximately at least about 7 seconds;

installing a foam plug comprising a reticulated fawn into the wounded segment of the pathway; and allowing the wounded segment of the pathway to heal with the foam plug installed.

23. A method of occluding the ovarian pathway of a female body, the ovarian pathway being characterized by an epithelial layer lining the inside of the ovarian pathway, a lamina propria layer surrounding the epithelial layer, a circular muscle layer surrounding the lamina propria layer and a longitudinal muscle layer surrounding the circular muscle layer, said method comprising the steps of:

applying a heating element to a target segment of the pathway, and operating the heating element to heat the target segment in the pathway;

limiting the heating of the target segment to avoid wounding the longitudinal layer by controlling the heating element to heat the target segment to a temperature range of 40–80° C. for a period of at least about 5 seconds;

installing a plug into the target segment of the pathway.

24. The method of claim 23 additionally comprising the step of providing the heating element in the form of at least one electrode adapted for application to the ovarian pathway.

25. The method of claim 24 additionally comprising the step of applying RF energy to the target segment through the electrode.

26. The method of claim 23 additionally comprising the step of providing the heating element in the form of at least two electrodes adapted for application to the ovarian pathway, and applying bi-polar RF energy to said electrodes.

27. The method of claim 23 additionally comprising the step of providing the heating element in the form of at least one resistive beating element adapted for application to the ovarian pathway.

28. The method of claim 23 additionally comprising the step of providing the heating element in the form of at least one microwave heating element adapted for application to the ovarian pathway.

29. The method of claim 23 additionally comprising the step of providing the heating element in the form of at least one ultrasound heating element adapted for application to the ovarian pathway.

30. The method of claim 23 additionally comprising the step of providing the heating element in the form of at least one laser heating element adapted for application to the ovarian pathway.

31. The method of claim 23 additionally comprising the step of providing the plug in the form of a reticulated foam plug having pores with pore sizes in the range of 40 to 200 microns.

32. The method of claim 23 additionally comprising the step of providing the plug in the form of a reticulated foam plug having pores with pore sizes in the range of 1 to 20 microns.

* * * * *

UNITED STATES PATENT AND TRADEMARK OFFICE
CERTIFICATE OF CORRECTION

PATENT NO. : 6,712,810 B2
DATED : March 30, 2004
INVENTOR(S) : Harrington et al.

It is certified that error appears in the above-identified patent and that said Letters Patent is hereby corrected as shown below:

<u>Title page,</u>
Item [75], Inventors, "Victoria E. Carr-Brendenl" should read -- Victoria E. Carr-Brendel --.

<u>Column 16,</u>
Line 13, the word "fawn" should read -- foam --;
Line 45, the word "beating" should read -- heating --.

Signed and Sealed this

Sixth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,712,810 B1
DATED : March 30, 2004
INVENTOR(S) : Arup Bhattacharyya It is certified that error appears in the above-identified patent and that said Letters Patent is hereby corrected as shown below:

Title page,
Item [56], References Cited, OTHER PUBLICATIONS, replace
"Kesan, V. et al. "High Performance 0,24$\mu$m p-MOSFETs" with -- Kesan, V. et al."
High Performance 0.25$\mu$m p-MOSFETs --; and replace
"Current. M.I. et al., "Atomic-Layer Cleaving with $Si_2Ge_1$," with -- Current, M.I. et al.,
"Atomic-Layer Cleaving with $Si_xGe_y$, --

Signed and Sealed this

Thirtieth Day of November, 2004

JON W. DUDAS
*Director of the United States Patent and Trademark Office*